US010190998B1

(12) United States Patent
Zhou et al.

(10) Patent No.: US 10,190,998 B1
(45) Date of Patent: Jan. 29, 2019

(54) METHOD AND DEVICE FOR EVALUATING AND PREDICTING A SHALE OIL ENRICHMENT AREAS OF FAULT LACUSTRINE BASINS

(71) Applicant: RESEARCH INSTITUTE OF PETROLEUM EXPLORATION & DEVELOPMENT, DAGANG OIL FIELD OF CNPC, Tianjin (CN)

(72) Inventors: Lihong Zhou, Tianjin (CN); Xianzheng Zhao, Tianjin (CN); Xiugang Pu, Tianjin (CN); Fengming Jin, Tianjin (CN); Wenya Jiang, Tianjin (CN); Dunqing Xiao, Tianjin (CN); Zhannan Shi, Tianjin (CN); Wenzhong Han, Tianjin (CN)

(73) Assignee: Research Institute Of Petroleum Exploration & Development, Dagang Oil Field Of CNPC, Tianjin (CN)

(*) Notice: Subject to any disclaimer, the term of this patent is extended or adjusted under 35 U.S.C. 154(b) by 0 days.

(21) Appl. No.: 16/116,244

(22) Filed: Aug. 29, 2018

(51) Int. Cl.
*G01N 23/2055* (2018.01)
*G01V 9/00* (2006.01)
(Continued)

(52) U.S. Cl.
CPC ......... *G01N 23/2055* (2013.01); *G01N 33/24* (2013.01); *G01N 33/28* (2013.01);
(Continued)

(58) Field of Classification Search
CPC .. G01N 23/20; G01N 23/205; G01N 23/2055; G01N 23/207; G01N 23/2076;
(Continued)

(56) References Cited

U.S. PATENT DOCUMENTS

| 5,155,546 A | 10/1992 | Balsam | |
|---|---|---|---|
| 7,538,319 B2 * | 5/2009 | Jacobi | G01V 5/104 250/269.6 |

(Continued)

FOREIGN PATENT DOCUMENTS

| CN | 104199121 A | 12/2014 |
|---|---|---|
| CN | 105243204 A | 1/2016 |

(Continued)

OTHER PUBLICATIONS

"Analysis of lithofacies characteristics and tight oil storage sweet spot in the fine-grained sedimentary area of the second member of the Cangdong sag" (English Abstract Provided).
(Continued)

*Primary Examiner* — Thomas R Artman
(74) *Attorney, Agent, or Firm* — Volpe and Koenig, P.C.

(57) ABSTRACT

A method is disclosed for evaluating and predicting a shale oil enrichment area of a fault lacustrine basin, comprising: obtaining materials and key data; determining a source-reservoir configuration relationship according to a longitudinal superposition relationship of different types of rock in a lithology profile and establishing a single-well lithofacies model; in the single-well lithofacies model, using a dolomite-to-formation ratio and a TOC average value to form a dolomite-to-formation ratio contour map and a TOC contour map, and superposing the dolomite-to-formation ratio contour map, the TOC contour map and a source-reservoir configuration relationship plane distribution map to form a lithofacies plane distribution map; on the basis of the lithofacies plane distribution map, superposing a vitrinite reflectance contour map and a dolomite thickness contour map to obtain a corresponding evaluation and prediction map of the shale oil enrichment area of the fault lacustrine basin.

10 Claims, 5 Drawing Sheets

(51) Int. Cl.
*G01N 33/24* (2006.01)
*G01N 33/28* (2006.01)

(52) U.S. Cl.
CPC ......... *G01V 9/00* (2013.01); *G01N 2223/056* (2013.01); *G01N 2223/1016* (2013.01); *G01N 2223/616* (2013.01)

(58) Field of Classification Search
CPC ......... G01N 2223/045; G01N 2223/05; G01N 2223/056; G01N 2223/302; G01N 2223/304; G01N 2223/401; G01N 2223/402; G01N 2223/405; G01N 2223/423; G01N 2223/426; G01N 2223/616; G01N 2223/633; G01N 2223/648; G01N 2223/649; G01V 5/0025
See application file for complete search history.

(56) References Cited

U.S. PATENT DOCUMENTS

| | | | | |
|---|---|---|---|---|
| 7,615,741 B2* | 11/2009 | Jacobi | ................ | G01V 5/104 250/269.1 |
| 8,049,164 B2* | 11/2011 | Kirkwood | ............ | G01V 5/101 250/262 |
| 8,618,472 B2* | 12/2013 | Suparman | ............ | G01V 5/101 250/252.1 |
| 9,851,468 B2* | 12/2017 | Herron | ................ | G01N 33/246 |
| 2008/0179509 A1* | 7/2008 | Jacobi | .................... | G01V 5/104 250/269.2 |
| 2008/0179510 A1* | 7/2008 | Jacobi | .................... | G01V 5/104 250/269.6 |
| 2009/0114806 A1* | 5/2009 | Kirkwood | ............. | G01V 5/101 250/269.6 |
| 2012/0091328 A1* | 4/2012 | Suparman | ............. | G01V 5/101 250/269.1 |
| 2013/0091925 A1* | 4/2013 | Darrah | .................... | G01V 5/06 73/23.35 |
| 2017/0045491 A1* | 2/2017 | Karoum | ................. | G01N 31/12 |
| 2017/0248011 A1* | 8/2017 | Craddock | ................ | G01N 9/36 |
| 2017/0315259 A1* | 11/2017 | Quirein | .................. | G01V 5/102 |

FOREIGN PATENT DOCUMENTS

| | | |
|---|---|---|
| CN | 106324228 A | 1/2017 |
| CN | 106503834 | 3/2017 |
| CN | 107102376 | 8/2017 |

OTHER PUBLICATIONS

Characteristics and evaluation factors of shale oil reservoir of the third member of Hetaoyun Formation, Palaeogene in Biyang Depression (English Abstract Provided).

* cited by examiner

METHOD AND DEVICE FOR EVALUATING AND PREDICTING A SHALE OIL ENRICHMENT AREAS OF FAULT LACUSTRINE BASINS

CROSS REFERENCE TO RELATED APPLICATIONS

This application is a U.S. counterpart of Chinese Application No. 201710386352.9, which was filed on May 26, 2017, was published Aug. 29, 2017 as CN 107102376, was entitled "Comprehensive evaluation and prediction method for enrichment favorable area of dense oil in lacustrine basin," and is incorporated herein by reference as if fully set forth.

FIELD OF THE INVENTION

The present invention relates to a method and device for evaluating and predicting a shale oil enrichment area of a fault lacustrine basin, belonging to the technical field of petroleum exploration.

BACKGROUND OF THE INVENTION

With the continuous improvement of conventional oil and gas exploration degree, the difficulty of exploration is increasing, and the cost of exploration is increasing day by day. Finding a new replacement field has become one of the important issues in oil and gas exploration today. Unconventional oil and gas, especially shale oil and gas, has the characteristics of rich oil and gas resources, large exploration potential and low exploration degree. With the continuous advancement of exploration technology and the deepening of understanding, shale oil and gas has become an important field of oil and gas replacement. Because the shale oil and gas is distributed in a large-area, low-abundance and dispersion manner in the fine-grained sedimentary area of semi-deep lakes/deep lakes, sweet spots are locally enriched, and the sweet spots have the typical characteristics of strong concealment, complicated distribution rules and difficulty in finding. Therefore, the current evaluation of shale oil and gas is mostly concentrated on the study of longitudinally distributed formation segments of single wells, while the comprehensive evaluation and prediction of planar sweet spots is less carried out, mainly focusing the qualitative finding of areas close to high-quality source rocks and having relatively high porosity, porosity and permeability, without comprehensive consideration of control factors such as the configuration relationship between the source rock and a reservoir, the thermal evolution of the source rock, and the thickness of the reservoir.

SUMMARY OF THE INVENTION

In order to solve the defects in the above-mentioned technology, the present invention relates to a method and device for evaluating and predicting a shale oil enrichment area of a fault lacustrine basin.

In order to solve the above technical problem, the technical solution employed in the present invention is: a method for evaluating and predicting a shale oil enrichment area of a fault lacustrine basin, generally comprising the following steps:

Step 1, obtaining analytical test materials for the key core well of the fine-grained facies region of the shale oil enrichment area of the fault lacustrine basin, and obtaining key data of the target stratum logging interpretation based on the analytical test material, wherein the key data of the target stratum logging interpretation includes a dolomite-to-formation ratio, dolomite thickness, a lithology profile, a TOC (Total Organic Carbon) average value, and effective source rock thickness;

Step 2: determining a source-reservoir configuration relationship according to a longitudinal superposition relationship of different types of rock in the lithology profile, and establishing a single-well lithofacies mode in conjunction with the dolomite-to-formation ratio and the TOC average value;

Step 3: in the single-well lithofacies mode, forming a dolomite-to-formation ratio contour map, a TOC contour map, and a source-reservoir configuration relationship plane distribution map respectively by using the dolomite-to-formation ratio, the TOC average value, and the source-reservoir configuration relationship, and superposing the dolomite-to-formation ratio contour map, the TOC contour map, and the source-reservoir configuration relationship plane distribution map to form a lithofacies plane distribution map; and Step 4: on the basis of the lithofacies plane distribution map, superposing a vitrinite reflectance contour map and a dolomite thickness contour map formed through the dolomite thickness to obtain a corresponding evaluation and prediction map of the shale oil enrichment area of the fault lacustrine basin.

Further, for Step 1, the analytical test material comprises an X-diffraction whole rock analysis main mineral component and TOC, and said obtaining key data of the target stratum logging interpretation based on the analytical test material comprises: establishing a first quantitative relationship between an "AC~DEN distance" and the X-diffraction whole rock analysis main mineral component and a second quantitative relationship between the "AC~DEN distance" and the TOC respectively; and applying the first quantitative relationship and the second quantitative relationship to each single well in the fine-grained facies region to obtain key data of the target stratum logging interpretation.

For the specific establishment method of the first quantitative relationship and the second quantitative relationship, reference may be made to the Chinese Patent Application No. CN201510404879.0, entitled "Lithology Identification Method", and the Chinese Patent Application No. CN201510419628.X, entitled "A Method for Determining Total Organic Carbon in Pulveryte".

The dolomite-to-formation ratio refers to a ratio of the cumulative thickness of dolomite to the thickness of a formation. The dolomite thickness refers to the sum of the thicknesses of the dolomite and the argillaceous dolomite. The lithology profile refers to the rock unit series for recording the stratigraphic sequences, lithology, thickness, fossils and interrelation of observed and measured formations, which reflects the variation rule of rock properties in the longitudinal direction. The TOC average value is, for example, the average value of the corresponding target stratum logging TOC for every 0.125 m data point. The effective source rock thickness refers to the sum of the thicknesses of argillaceous shale and dolomitic mudstone.

Further, for Step 2, the different types of rock in the lithology profile include dolomite, argillaceous dolomite, dolomitic mudstone and argillaceous shale, and the source-reservoir configuration relationship refers to the longitudinal superposition relationship between source rock (mudstone)

and a reservoir formation (dolomite), mainly including three types: multi-layer type, interbedded type, and sandwich type.

Further, Step 2 also comprises determining the lithofacies type of each single well in conjunction with the dolomite-to-formation ratio and the TOC average value.

Further, Step 4 may also comprise: based on the evaluation and prediction map of the shale oil enrichment area of the fault lacustrine basin, dividing the sweet spots of shale oil and distribution areas.

In order to solve the above technical problem, the present invention further adopts the following technical solution:

a comprehensive evaluation device for a shale oil enrichment area of a fault lacustrine basin, comprising: a processor. The processor is configured to: obtain analytical test material for a key core well in a fine-grained facies region of the shale oil enrichment area of the fault lacustrine basin, and obtain key data of the target stratum logging interpretation based on the analytical test material, wherein the key data of the target stratum logging interpretation includes a dolomite-to-formation ratio, dolomite thickness, a lithology profile, a TOC average value, and effective source rock thickness; determining a source-reservoir configuration relationship according to a longitudinal superposition relationship of different types of rock in the lithology profile, and establishing a single-well lithofacies mode in conjunction with the dolomite-to-formation ratio and the TOC average value; in the single-well lithofacies mode, form a dolomite-to-formation ratio contour map, a TOC contour map, and a source-reservoir configuration relationship plane distribution map respectively by using the dolomite-to-formation ratio, the TOC average value, and the source-reservoir configuration relationship, and superpose the dolomite-to-formation ratio contour map, the TOC contour map and the source-reservoir configuration relationship plane distribution map to form a lithofacies plane distribution map; and on the basis of the lithofacies plane distribution map, superpose a vitrinite reflectance contour map and a dolomite thickness contour map formed through the dolomite thickness to obtain a corresponding evaluation and prediction map of the shale oil enrichment area of the fault lacustrine basin.

Further, the analytical test material comprises an X-diffraction whole rock analysis main mineral component and TOC, and said key data of the target stratum logging interpretation based on the analytical test material comprises: establishing a first quantitative relationship between an "AC~DEN distance" and the X-diffraction whole rock analysis main mineral component and a second quantitative relationship between the "AC~DEN distance" and the TOC respectively; and applying the first quantitative relationship and the second quantitative relationship to each single well in the fine-grained facies region to obtain key data of the target stratum logging interpretation.

Further, the different types of rock include dolomite, argillaceous dolomite, dolomitic mudstone and argillaceous shale.

Further, the processor is also configured to: determine the lithofacies type of each single well in conjunction with the dolomite-to-formation ratio and the TOC average value.

Further, the processor is also configured to: based on the evaluation and prediction map of the shale oil enrichment area of the fault lacustrine basin, divide the sweet spots of shale oil and distribution areas.

Compared with the prior art, the present invention has the following beneficial effects:

1) the first quantitative relationship between an "AC~DEN distance" and the X-diffraction whole rock analysis main mineral component and the second quantitative relationship between the "AC~DEN distance" and the TOC are used to carry out the identification and division method of lithology and the logging method for dividing organic matter abundance of the source rock; the characteristics of simple operation and high accuracy are achieved, and the formed lithology profile can identify the type of source-reservoir configuration relationship;

2) from the lithofacies plane distribution map formed by superposing the dolomite-to-formation ratio contour map, the TOC contour map and the source-reservoir configuration relationship plane map, the plane distribution rule of high-quality reservoirs and high-quality source rock and mutual configuration relationship thereof can be clearly, comprehensively, and effectively reflected; and 3) from the evaluation and prediction map of the shale oil enrichment area of the fault lacustrine basin formed by superposing a vitrinite reflectance contour map and a dolomite thickness contour map on the basis of the lithofacies plane distribution map, the distribution regions and distribution areas of different types of shale oil sweet spots, favorable reservoir thickness, and other information can be clearly reflected.

In summary, the method and device of the present invention have the advantages of low economic cost, high operability and high accuracy, and can provide theoretical and cognitive support for the optimization of the favorable region of the shale oil of the fault lacustrine basin and the deployment of the well locations.

Other features and advantages of the present invention will be described in detail in the following specific embodiments.

DETAILED DESCRIPTION OF THE EMBODIMENTS

The present invention will be further described in detail with reference to the accompanying drawings and specific embodiments.

The Ek2 of Cangdong Sag of Huanghua Depression in the Bohai Bay Basin is the main formation for Hydrocarbon layer system in the area. The core and logging mainly shows dark gray and gray-black (oil) lacustrine shales. This area, featuring a wide horizontal distribution range and large longitudinal formation thickness, has geological conditions for forming large-area contiguous distribution of shale oil. In recent years, many oil wells in the middle part of the Palaeo-lacustrine basin at the lower part of the slope of the Ek2 of Cangdong Sag have obtained industrial oil flow in the fine-grained sedimentary area, which has become an important replacement for future oil and gas exploration. Hereinafter, the method and device of the present invention will be described in detail by taking the fifth-order sequence Ek22SQ⑥ of the Ek2 of Cangdong Sag as an exemplary implementation object.

Embodiment 1

Figure 1:
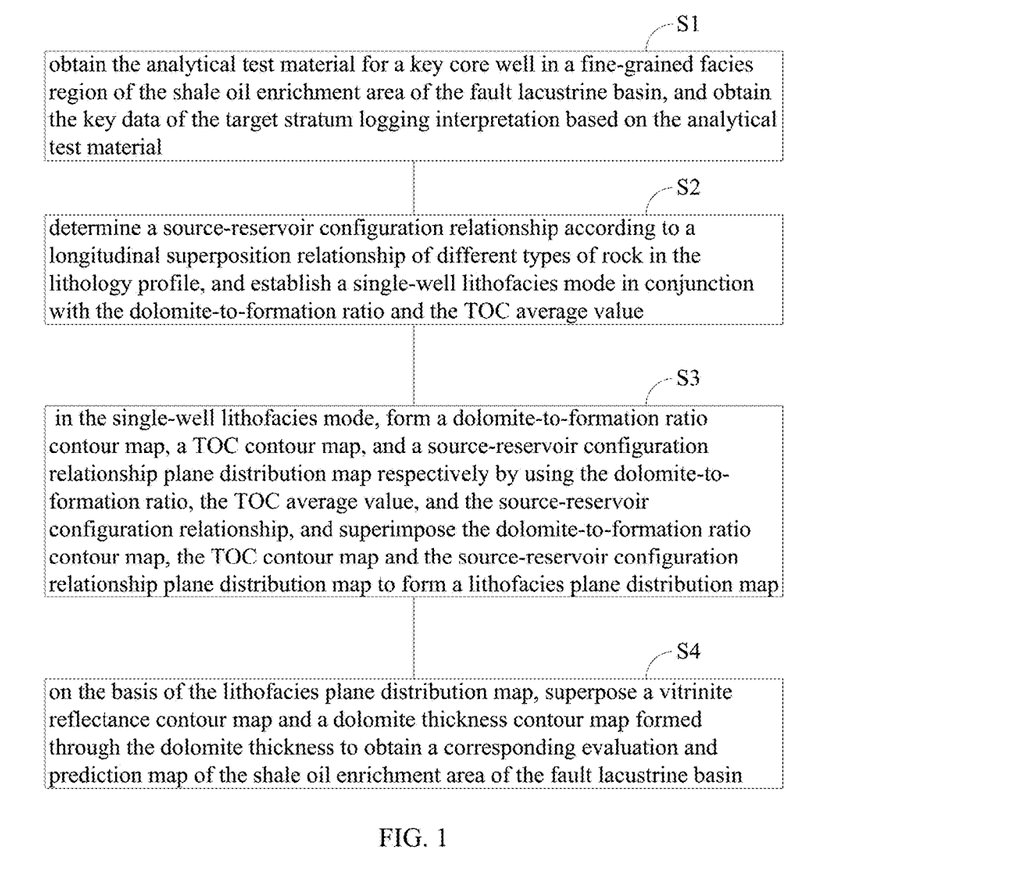
FIG. 1 is an overall flow chart of a method for evaluating and predicting a shale oil enrichment area of a fault lacustrine basin according to an embodiment of the present invention.

As shown in FIG. 1, the present embodiment provides a method for evaluating and predicting a shale oil enrichment area of a fault lacustrine basin, generally comprising the following steps:

Step S1 is to obtain analytical test material for a key core well in a fine-grained facies region of the shale oil enrichment area of the fault lacustrine basin, and obtain key data of the target stratum logging interpretation based on the analytical test material.

Herein, the key data of the target stratum logging interpretation includes a dolomite-to-formation ratio, dolomite thickness, a lithology profile, a TOC average value, and effective source rock thickness.

Step S2 is to determine a source-reservoir configuration relationship according to a longitudinal superposition relationship of different types of rock in the lithology profile, and establish a single-well lithofacies mode in conjunction with the dolomite-to-formation ratio and the TOC average value.

Step S3 is to, in the single-well lithofacies mode, form a dolomite-to-formation ratio contour map, a TOC contour map, and a source-reservoir configuration relationship plane distribution map respectively by using the dolomite-to-formation ratio, the TOC average value, and the source-reservoir configuration relationship, and superpose the dolomite-to-formation ratio contour map, the TOC contour map and the source-reservoir configuration relationship plane distribution map to form a lithofacies plane distribution map.

Step S4 is to, on the basis of the lithofacies plane distribution map, superpose a vitrinite reflectance contour map and a dolomite thickness contour map formed through the dolomite thickness to obtain a corresponding evaluation and prediction map of the shale oil enrichment area of the fault lacustrine basin.

Specifically, for Step S1: the key core well, Well G108-8, is located at the lower part of the west slope of the Ek2 of the Cangdong Sag. The Ek2 of the Cangdong Sag of the well is continuously cored for nearly 500 m, and is divided into 10 fifth-order sequences from bottom to top, such as Ek24SQ① and Ek24SQ②. The core material reveals that Ek24SQ① and Ek22SQ⑧ are tight sandstone sections, and the non-sandstone sections are mainly gray-black and dark-gray shale (oil shale) with a small amount of thin-layer pure taupe and brown dolomite in which local enrichment of sandy strips and sandy masses can be seen.

The rich and detailed analytical test material is available for the core section. It is designed so that there are more than 1000 samples for whole rock X-diffraction and TOC testing. By establishing quantitative relationships between "AC~DEN distance" and X-diffraction whole rock analysis main mineral components and between the "AC~DEN distance" and the TOC, fitting formulas are respectively formed to interpret the lithology and TOC based on the "AC~DEN distance"; the "AC~DEN distance" fitting formulas are applied to all single wells in the fine-grained sedimentary area (more than 70 wells in the drilling target stratum); on a geological work platform (for example, the Reform GeoOffice), the logging interpretation lithology profiles and the TOC changing curves (formed by connecting the scatter points at intervals of 0.125 m) of all single wells Ek22SQ⑥ are obtained and based on this, the dolomite-to-formation ratios, dolomite thicknesses, TOC average values, effective source rock thicknesses and other key data of all the single wells Ek22SQ⑥ can be obtained through statistics.

For Step S2, the longitudinal superposition combination relationships of dolomite and mudstone are observed according to the logging interpretation lithology profiles, source-reservoir ratios and dolomite-to-formation ratios of the single wells Ek22SQ⑥, and finally three source-reservoir configuration relationships (multi-layer type, inter-bedded type, and sandwich type) are defined.

Figure 2:
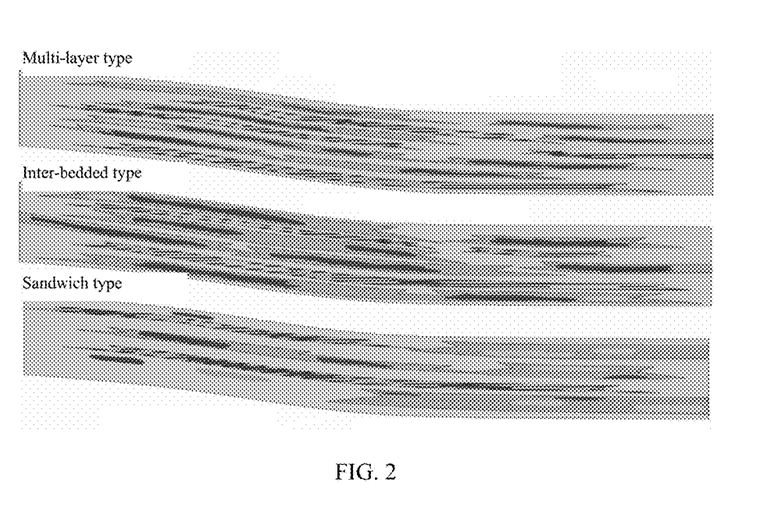
FIG. 2 is a schematic diagram of source-reservoir configuration relationship according to an embodiment of the present invention.

As shown in FIG. 2, multi-layer type: the source-reservoir ratio is 0.7-1.5, the dolomite-to-formation ratio is 40-60%, and the thin-layer reservoir and the thin-layer source rock frequently intersect each other, and hydrocarbons generated by the thermal evolution of the source rock move to adjacent reservoirs; these types of reservoirs are thin and large in quantity, small in scale for each single layer, and have a single layer thickness distribution less than 1 m, but large cumulative thickness.

Inter-bedded type: the source-reservoir ratio is 0.7-1.5, the dolomite-to-formation ratio is 40-60%, medium-thick source rock and medium-thick reservoirs are in longitudinal superimposed distribution; hydrocarbons generated by the thermal evolution of the source rocks can also easily move to adjacent reservoirs, and have a single layer thickness distribution of 1-2 m.

Sandwich type can be subdivided into two categories. The first category: the source-reservoir ratio is less than 0.7, and the dolomite-to-formation ratio is greater than 60%; the medium-thin shale is sandwiched between massive dolomite and argillaceous dolomite (single-layer thickness is greater than 2 m); due to relatively thin source rock, the amount of hydrocarbons generated is small; although the dolomite reservoirs are relatively well developed, they can only form lean or even oil-free dry formations; the small amount of oil and gas produced by the thin source rock is only charged into the adjacent reservoirs. The second category: the source-reservoir ratio is greater than 1.5, and the dolomite-to-formation ratio is less than 40%; the medium-thin shale is sandwiched in massive mudstone (single-layer thickness is greater than 2 m); hydrocarbons generated are abundant, but good reservoirs are in shortage; even though the thin reservoirs have good oil-bearing properties, they have less thickness, resulting in considerable residual hydrocarbons in the shale, and locally meeting conditions for forming shale oil sweet spots.

Figure 3:
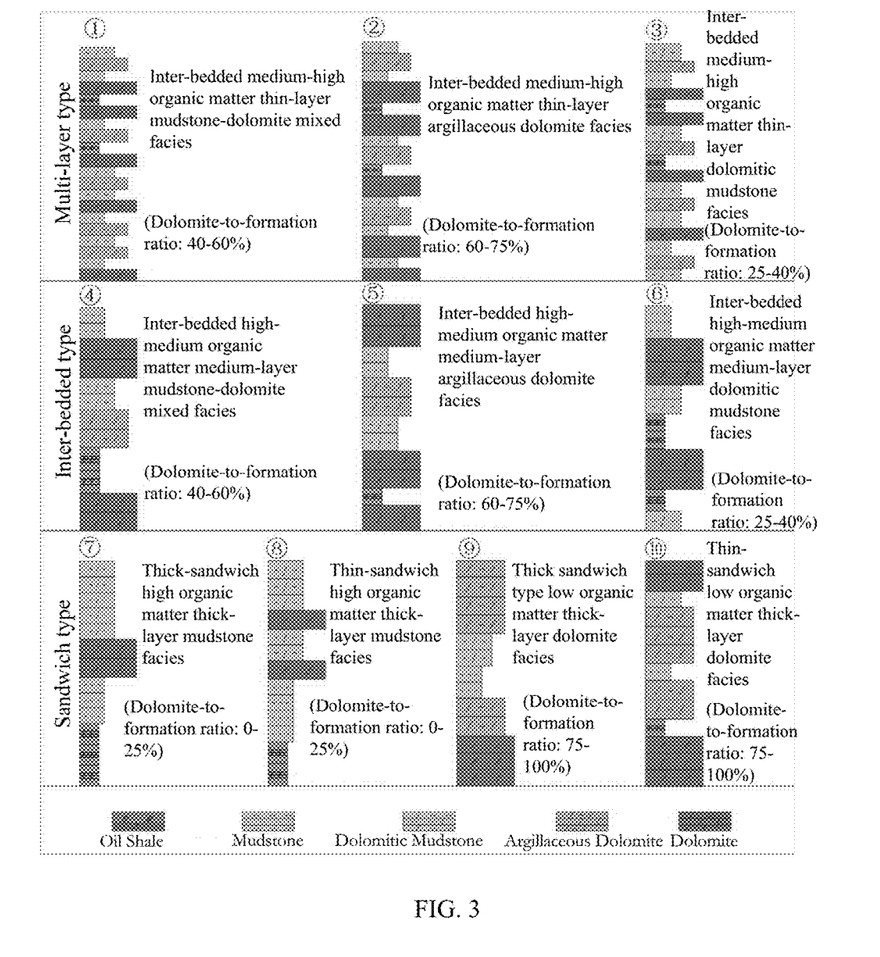
FIG. 3 is a schematic diagram of lithofacies types according to an embodiment of the present invention.
Figure 5:
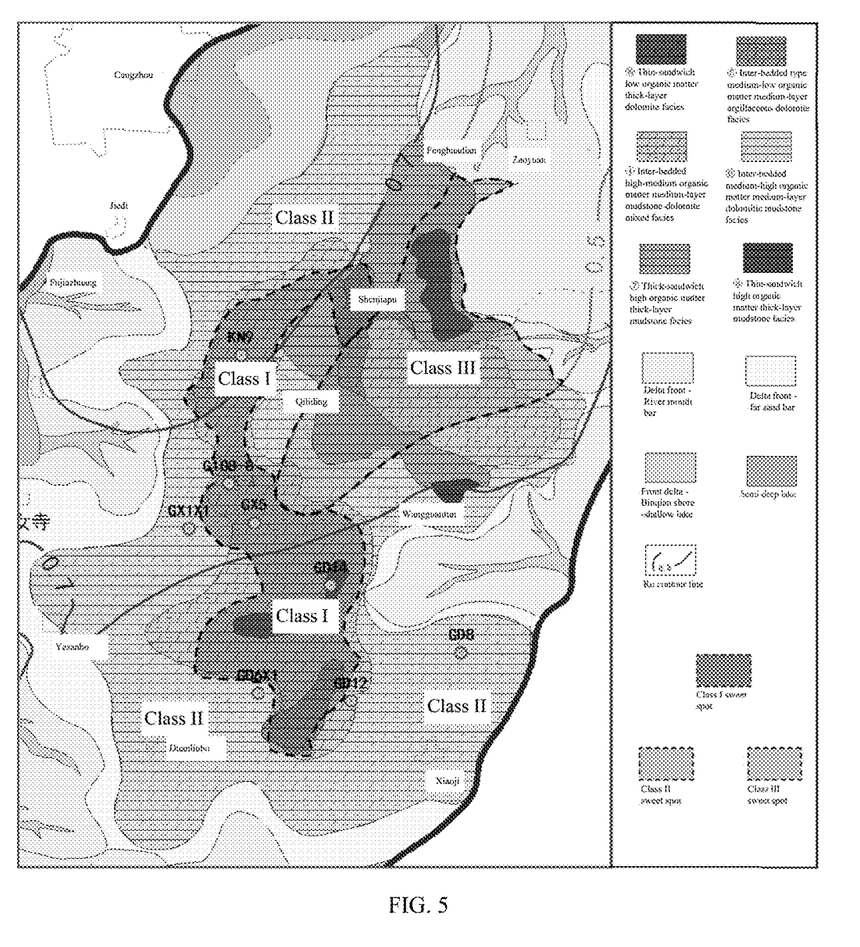
FIG. 5 is an evaluation and prediction map of an exemplary shale oil sweet spots according to an embodiment of the present invention.

The division rules and standards of the lithofacies are shown in Table 1. According to the dolomite-to-formation ratio, the main-class lithofacies of a stratigraphic unit or sequence are named by the dominant lithofacies. On the basis of the main-class lithofacies, in conjunction with the abundance of organic matter, a subfacies is formed, namely: "organic facies+dominant facies", such as: "high-organic-matter dolomitic mudstone facies". On the basis of subfacies division, in conjunction with the source-reservoir configuration relationship, a small-class facies is formed, namely: "stratigraphic facies+organic facies+dominant facies", such as: "multi-layer type medium-high organic matter thin-layer argillaceous dolomite facies". According to the needs of actual research accuracy, drawings are plotted according to different facies such as main-class facies, subfacies or small-class facies. Taking the small-class facies with the highest drawing accuracy as an example, from the Ek22SQ⑥ in the Ek2 of Cangdong Sag of Huanghua Depression, 10 types of lithofacies such as the medium-high organic matter thin-layer mudstond-dolomite mixed phase, inter-bedded high-medium organic matter medium-layer mudstond-dolomite mixed facies, inter-bedded medium-low organic matter medium-layer argillaceous dolomite, can be identified, and the lithofacies mode of this area is finally established, as shown in FIG. 3.

the dolomite thickness contour map, so as to evaluate and predict the shale oil enrichment area. Considering the various control factors of shale oil enrichment, Ek2²SQ⑥ can be divided into 3 classes (I, II and III) of shale oil sweet spots (FIG. 5): sweet spots of Class I belong to the source/reservoir neighboring shale oil, with the main lithofacies type of inter-bedded medium-low organic matter medium-layer argillaceous dolomite facies, in which reservoirs are

TABLE 1

| No. | Rock type | Dominant facies Dolomite-to-formation ratio/% | Organic facies Abundance of organic matter | TOC/% | Stratigraphic facies Source-reservoir configuration relationship | Stratigraphic facies Logging interpretation single-layer thickness | Lithofacies type Main class Dominant facies | Sub class Organic facies + dominant facies | Small class Stratigraphic facies + organic facies + dominant facies |
|---|---|---|---|---|---|---|---|---|---|
| 1 | Dolomite facies | >75 | High organic matter | >4 | Sandwich type | Medium-thin layer sandwiched in thick layer (>2 m) | Such as: dolomite facies, argillaceous dolomite facies, dolomitic mudstone facies, argillaceous shale facies | Such as: high organic matter dolomitic mudstone facies | Such as: multi-layer medium-high organic matter thin-layer argillaceous dolomite facies |
| 2 | Argillaceous dolomite facies | 50-75 | | | | | | | |
| 3 | Dolomitic mudstone facies | 25-50 | Medium Organic matter | 2-4 | Inter-bedded type | Medium layer (1-2 m) | | | |
| 4 | Mudstone facies | <25 | Low organic matter | <2 | Multi-layer type | Thin layer (<1 m) | | | |

Figure 4:
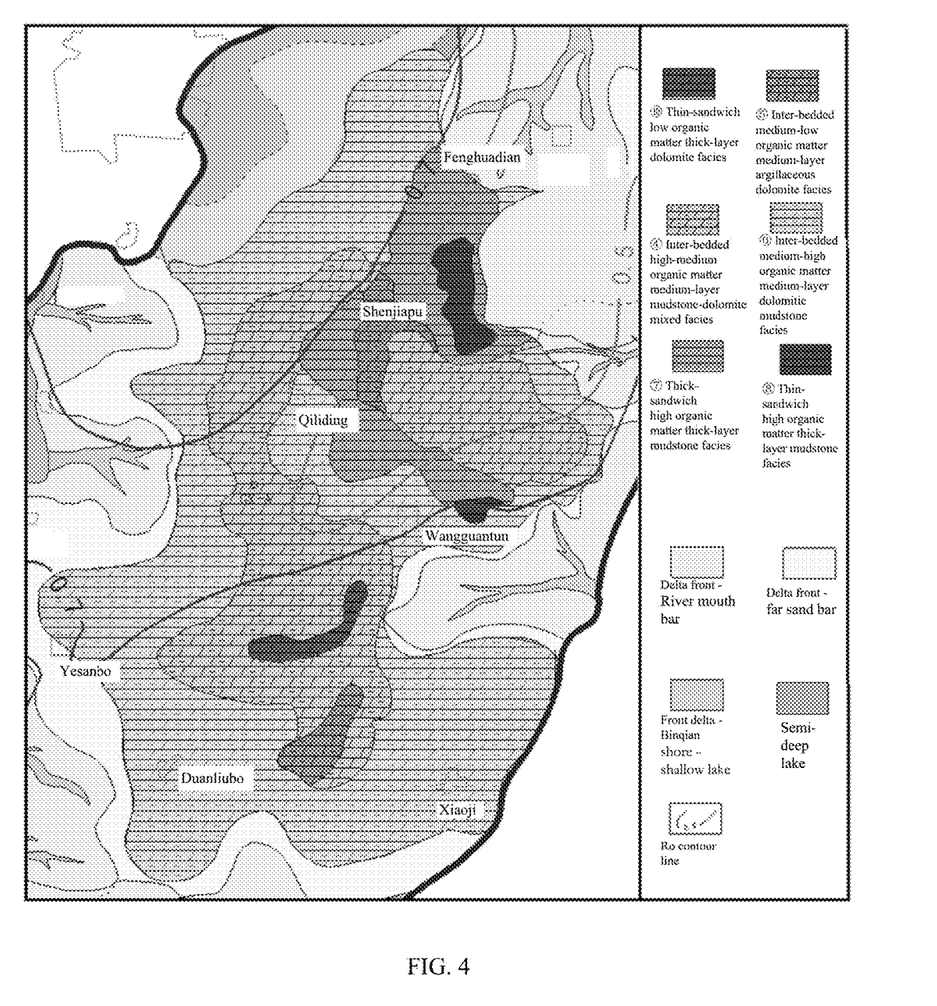
FIG. 4 is a diagram of an exemplary lithofacies plane distribution map according to an embodiment of the present invention.

For Step S3, all the calculated single-well dolomite-to-formation ratio data of the Ek2²SQ⑥ is applied to the plane graph to form a dolomite-to-formation ratio contour map, and the calculated TOC average values of all single wells are applied to the plane graph to form a TOC contour map. At the same time, all the calculated source-reservoir configuration relationships of the single wells are applied to the plane graph to form a source-reservoir configuration plane distribution map. The dolomite-to-formation ratio contour map, the TOC contour map and the source-reservoir configuration relationship plane distribution map are superimposed. According to the different plane combinations of the dolomite-to-formation ratio, TOC, and source-reservoir configuration in Table 1 and FIG. 3, the plane distribution map of small-class facies is formed, as shown in FIG. 4, for example, in the plane distribution area of inter-bedded medium-low organic matter middle-layer argillaceous dolomite facies, the dolomite-to-formation ratio contours are mainly distributed in the range of 50-75%, the TOC contours are distributed in the range of less than 4%, and the source-reservoir configuration relationships are dominated by inter-bedded type. Ek2²SQ⑥ is mainly composed of six facies types such as inter-bedded medium-low organic matter medium-layer argillaceous dolomite facies and inter-bedded high-medium organic matter medium-layer mudstond-dolomite mixed facies. The facies plane distribution map can reflect the plane distribution of the main reservoirs (dolomite) and the plane distribution of the main source rock (mudstone), and can reflect the distribution rule of different source-reservoir configuration relationships in the plane.

For Step S4, based on the plane distribution map of Ek2²SQ⑥ in FIG. 4, a thermal evolution maturity Ro contour map is superimposed on it to obtain the corresponding evaluation and prediction map of the shale oil enrichment area of the fault lacustrine basin in conjunction with mainly dolomite, the dolomite-to-formation ratio is mainly distributed in the range of 50-75%, Ro is above 0.5%, and the average TOC is mainly distributed in the range of 1-3%, the average thickness of dolomite is more than 15 m, and the distribution area is about 106 km²; the sweet spots of Class II also belong to the source/reservoir neighboring shale oil, with the main lithofacies type of inter-bedded medium-high organic matter medium-layer dolomitic mudstone facies, in which reservoirs are mainly dolomitic mudstone, the dolomite-to-formation ratio is mainly distributed in the range of 25-50%, Ro is above 0.5%, and the TOC is mainly distributed in the range of 2-3.5%, the average thickness of dolomitic mudstone is 12 m, and the distribution area is about 165 km²; the sweet spots of Class III also belong to the source/reservoir neighboring shale oil and source/reservoir integrated shale oil, with relatively low thermal evolution maturity, in which Ro is basically distributed in the range above 0.5%, reservoirs are mainly dolomite and argillaceous shale with relatively low maturity, the dolomite-to-formation ratio is mainly distributed in the range of 15-70%, the TOC is mainly distributed in the range of 2-4%, and the distribution area is about 35 km².

According to the research results of the present invention, multiple pre-exploration wells are deployed in the class I sweet spot, and industrial oil flows are obtained in wells such as G108-8, KN9, GD6×1, which further confirms the reliability of the comprehensive evaluation and prediction method of the shale oil enrichment area of the fault lacustrine basin. Under the current economic and technical conditions, the prediction accuracy of the method can meet the needs of shale oil exploration.

Embodiment 2

This embodiment provides a comprehensive evaluation and prediction device for a shale oil enrichment area of a fault lacustrine basin, comprising: a processor. The processor is configured to: obtain analytical test material for a key core well in a fine-grained facies region of the shale oil enrichment area of the fault lacustrine basin, and obtain key data of the target stratum logging interpretation based on the analytical test material, wherein the key data of the target stratum logging interpretation includes a dolomite-to-formation ratio, dolomite thickness, a lithological profile, a TOC average value, and effective source rock thickness; determine a source-reservoir configuration relationship according to a longitudinal superposition relationship of different types of rock in the lithological profile, and establish a single-well lithofacies mode in conjunction with the dolomite-to-formation ratio and the TOC average value; in the single-well lithofacies mode, form a dolomite-to-formation ratio contour map, a TOC contour map, and a source-reservoir configuration relationship plane distribution map respectively by using the dolomite-to-formation ratio, the TOC average value, and the source-reservoir configuration relationship, and superpose the dolomite-to-formation ratio contour map, the TOC contour map and the source-reservoir configuration relationship plane distribution map to form a lithofacies plane distribution map; and on the basis of the lithofacies plane distribution map, superpose a vitrinite reflectance contour map and a dolomite thickness contour map formed through the dolomite thickness to obtain a corresponding evaluation and prediction map of the shale oil enrichment area of the fault lacustrine basin.

The processor is also configured to: based on the comprehensive evaluation and prediction of the shale oil enrichment area, divide the sweet spot types of shale oil and distribution areas.

The processor is also configured to: based on the evaluation and prediction map of the shale oil enrichment area of the fault lacustrine basin, divide the sweet spot types of shale oil and distribution areas.

It should be noted that the specific implementation details of Embodiment 2 can be referred to the foregoing Embodiment 1, and its details are not described herein again.

Those skilled in the art can understand that all or part of the steps for implementing the methods in the above embodiments may be completed by related hardware under the instructions of a program, and the program is stored in a storage medium, and includes a plurality of instructions for enabling a single-chip processor, a chip, or a processor to perform all or part of the steps of the methods described in the various embodiments of the present application. The foregoing storage medium includes: a U disk, a mobile hard disk, a read-only memory (ROM), a random access memory (RAM), a magnetic disk, or an optical disk, and the like, which can store program codes.

The above embodiments are not intended to limit the present invention, and the present invention is not limited to the above examples, and variations, modifications, additions or substitutions made by those skilled in the art within the scope of the technical solutions of the present invention also fall within the scope of protection of the present invention.

The invention claimed is:

1. A method for evaluating and predicting a shale oil enrichment area of a fault lacustrine basin, wherein the method comprising:

Step 1, obtaining analytical test material for a key core well in a fine-grained facies region of the shale oil enrichment area of the fault lacustrine basin, and obtaining key data of the target stratum logging interpretation based on the analytical test material, wherein the key data of the target stratum logging interpretation includes a dolomite-to-formation ratio, dolomite thickness, a lithology profile, a total organic carbon (TOC) average value, and effective source rock thickness;

Step 2, determining a source-reservoir configuration relationship according to a longitudinal superposition relationship of different types of rock in the lithology profile, and establishing a single-well lithofacies mode in conjunction with the dolomite-to-formation ratio and the TOC average value;

Step 3, in the single-well lithofacies mode, forming a dolomite-to-formation ratio contour map, a TOC contour map and a source-reservoir configuration relationship plane distribution map respectively by using the dolomite-to-formation ratio, the TOC average value and the source-reservoir configuration relationship, and superposing the dolomite-to-formation ratio contour map, the TOC contour map and the source-reservoir configuration relationship plane distribution map to form a lithofacies plane distribution map; and Step 4: on the basis of the lithofacies plane distribution map, superposing a vitrinite reflectance contour map and a dolomite thickness contour map formed through the dolomite thickness to obtain a corresponding evaluation and prediction map of the shale oil enrichment area of the fault lacustrine basin.

2. The method for evaluating and predicting a shale oil enrichment area of a fault lacustrine basin according to claim 1, wherein the analytical test material comprises an X-diffraction whole rock analysis main mineral component and TOC, and in Step 1, obtaining the key data of the target stratum logging interpretation based on the analytical test material comprises:

establishing a first quantitative relationship between an "AC~DEN distance" and the X-diffraction whole rock analysis main mineral component and a second quantitative relationship between the "AC~DEN distance" and the TOC respectively; and applying the first quantitative relationship and the second quantitative relationship to each single well in the fine-grained facies region to obtain the key data of the target stratum logging interpretation.

3. The method for evaluating and predicting a shale oil enrichment area of a fault lacustrine basin according to claim 1, wherein the different types of rock include dolomite, argillaceous dolomite, dolomitic mudstone and argillaceous shale.

4. The method for evaluating and predicting a shale oil enrichment area of a fault lacustrine basin according to claim 1, wherein Step 2 further comprises: determining the lithofacies type of each single well in conjunction with the dolomite-to-formation ratio and the TOC average value.

5. The method for evaluating and predicting a shale oil enrichment area of a fault lacustrine basin according to claim 1, wherein Step 4 further comprises:

dividing the sweet spots of shale oil and distribution areas based on the evaluation and prediction map of the shale oil enrichment area of the fault lacustrine basin.

6. A comprehensive evaluation device for a shale oil enrichment area of a fault lacustrine basin, wherein the device comprises:

a processor, configured to:

obtain analytical test material for a key core well in a fine-grained facies region of the shale oil enrichment area of the fault lacustrine basin, and obtain key data of the target stratum logging interpretation based on the analytical test material, wherein the key data of the target stratum logging interpretation includes a dolomite-to-formation ratio, dolomite thickness, a lithology profile, a TOC average value, and effective source rock thickness;

determine a source-reservoir configuration relationship according to a longitudinal superposition relationship of different types of rock in the lithology profile, and establish a single-well lithofacies mode in conjunction with the dolomite-to-formation ratio and the TOC average value;

in the single-well lithofacies mode, form a dolomite-to-formation ratio contour map, a TOC contour map, and a source-reservoir configuration relationship plane distribution map respectively by using the dolomite-to-formation ratio, the TOC average value, and the source-reservoir configuration relationship, and superpose the dolomite-to-formation ratio contour map, the TOC contour map and the source-reservoir configuration relationship plane distribution map to form a lithofacies plane distribution map; and on the basis of the lithofacies plane distribution map, superpose a vitrinite reflectance contour map and a dolomite thickness contour map formed through the dolomite thickness to obtain a corresponding evaluation and prediction map of the shale oil enrichment area of the fault lacustrine basin.

7. The comprehensive evaluation device for a shale oil enrichment area of a fault lacustrine basin according to claim 6, wherein the analytical test material comprises an X-diffraction whole rock analysis main mineral component and TOC, and obtaining the key data of the target stratum logging interpretation based on the analytical test material comprises:

establishing a first quantitative relationship between an "AC~DEN distance" and the X-diffraction whole rock analysis main mineral component and a second quantitative relationship between the "AC~DEN distance" and the TOC respectively; and applying the first quantitative relationship and the second quantitative relationship to each single well in the fine-grained facies region to obtain the key data of the target stratum logging interpretation.

8. The comprehensive evaluation device for a shale oil enrichment area of a fault lacustrine basin according to claim 6, wherein the different types of rock include dolomite, argillaceous dolomite, dolomitic mudstone and argillaceous shale.

9. The comprehensive evaluation device for a shale oil enrichment area of a fault lacustrine basin according to claim 6, wherein the processor is further configured to:

determine the lithofacies type of each single well in conjunction with the dolomite-to-formation ratio and the TOC average value.

10. The comprehensive evaluation device for a shale oil enrichment area of a fault lacustrine basin according to claim 6, wherein the processor is further configured to: divide the sweet spots of shale oil and distribution areas based on the evaluation and prediction map of the shale oil enrichment area of the fault lacustrine basin.

* * * * *